United States Patent [19]

Stenning

[11] 4,268,169
[45] May 19, 1981

[54] FLAW DETECTION PROBE FOR CYLINDRICAL BORES

[76] Inventor: Charles Stenning, 671 Enchanted Way, Pacific Palisades, Calif. 90272

[21] Appl. No.: 30,093

[22] Filed: Apr. 16, 1979

[51] Int. Cl.³ .............................................. G01B 11/22
[52] U.S. Cl. ................................................... 356/241
[58] Field of Search ........................................ 356/241

[56] References Cited

U.S. PATENT DOCUMENTS 3,761,186  9/1973  Wason .
4,135,824  1/1979  Jones .................................. 356/241

Primary Examiner—Craig E. Church
Attorney, Agent, or Firm—William C. Babcock

[57] ABSTRACT

A probe assembly for detecting flaws in cylindrical openings comprises a cylindrical probe having a sectional dimension conformed to be received in the interior of the opening inspected, the probe having a polished end aligned on a forty-five degree angle relative the probe axis to reflect the images of the sides of the opening. The probe is supported in a spring biased mount assembly advanced axially by way of a cam and advanced in rotation by a beveled gear arrangement on the interior of the bore.

6 Claims, 4 Drawing Figures

FLAW DETECTION PROBE FOR CYLINDRICAL BORES

BACKGROUND OF THE INVENTION

1. Field of the Invention

The present invention relates to viewing devices, and more particularly to reflective probes adapted for insertion into cylindrical bores.

2. Description of the Prior Art

In many applications inspection of the lateral walls of circular openings is desired, often entailing the examination of microscopic bores formed in electronic circuit boards. Such inspection is quite often best performed optically either through microscopic enlargement or through the measurement of the reflectivity of the wall. In each instance the course of such inspection entailed the insertion of probes which in themselves created a larger risk of damage to the bore walls than the damage or flaws detected.

Thus, examination of delicate electronic instruments and particularly examination of through plated holes in printed circuit boards has been heretofore relegated to post assembly tests or has been achieved with very elaborate and expensive viewing devices not practical in commercial use. The physical constraints, furthermore, entailed in examining a small opening are equally applicable to the examination process of high precision bores like the cylinder bores of an internal combustion engine. In each instance accurate axial alignment with the bore center is necessary and full rotational freedom is required in order to inspect all of the bore surface. Both in the microscopic opening and in the larger bores accurate advancement of the viewing instrument is necessary in order to both locate the flaw and determine the magnitude thereof. It is towards these ends that the present invention is erected. The features thereof being usable regardless of scale and regardless of the function or end use to which the inspected bore is put.

SUMMARY OF THE INVENTION

Accordingly, it is the general purpose and object of the present invention to provide an optical viewing device adapted for controlled insertion into the interior of cylindrical bores.

Other objects of the invention are to provide a viewing device which includes means for axial and radial alignment thereof within the confines of a bore.

Yet further objects of the invention are to provide a viewing device conformed for insertion into a bore and including means for either manual or automatic manipulation thereof.

Briefly these and other objects are accomplished within the present invention by providing a cylindrical probe having one end thereof cut along a bias or a forty-five degree angle to form an incline mirror surface. This cylindrical probe may be inserted into the interior of a bore and will thus provide a reflective surface through which the bore walls may be viewed. In order to allow for accurate manipulation of this cylindrical probe both along the bore axis and in angle it is installed onto a mount assembly including a spring loaded mount supported on a rotatable cam surface, the mount being further provided with a collar geared to a set of beveled gears for angular articulation. Thus, the vertical position of the mount and the probe installed thereon may be controlled by the rotation of the cam while the azimuth of the mirror surface at the end of the probe may be selected by the rotation of the bevel gears. The foregoing assembly may be provided with either manual or servo actuated controls and may be deployed in a calibrated fixture provided with a microscope for viewing the mirror surface.

By virtue of the foregoing features, accurate alignment of the probe end is achieved and the bore may be inspected along the stations thereof for the existence of flaws.

DESCRIPTION OF THE SPECIFIC EMBODIMENT

Figure 1:
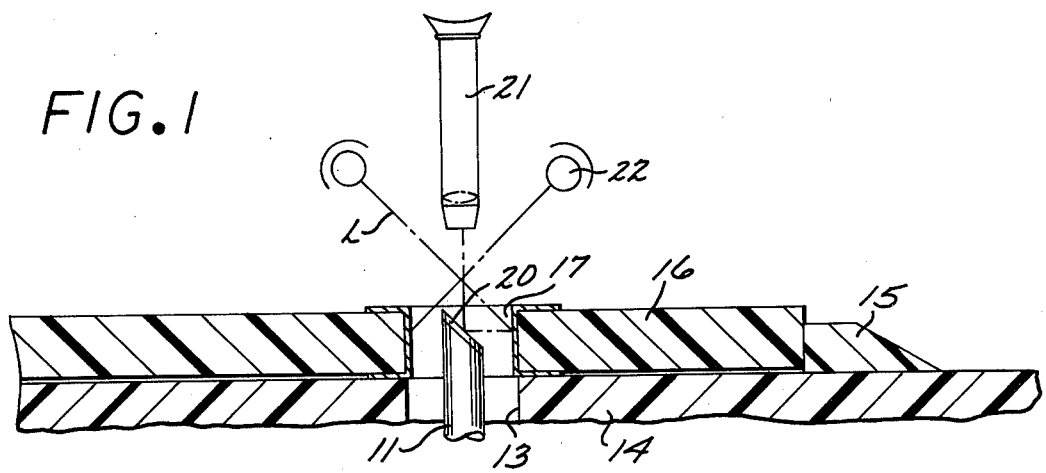
FIG. 1 is a detail view, in section, illustrating the use of a cylindrical probe constructed according to the present invention.
Figure 2:
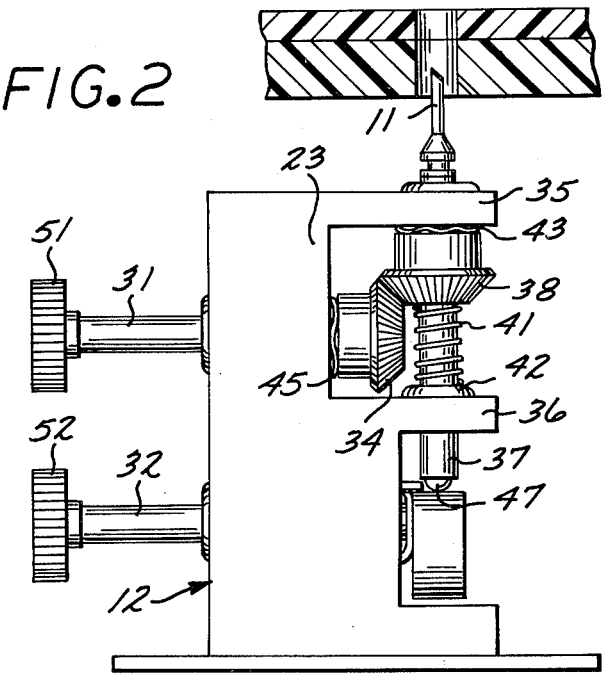
FIG. 2 is a side view of an inventive mount assembly adapted to articulate the cylindrical probe.
Figure 3:
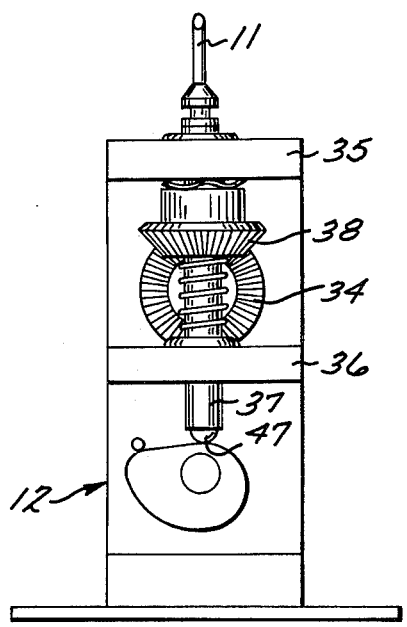
FIG. 3 is a front view of the mount assembly shown in FIG. 2.

As shown in FIGS. 1-3 the inventive flaw detector, generally designated by the numeral 10, comprises a cylindrical probe 11 extending vertically from a mount assembly 12 into the interior of an opening 13 formed in a platform 14. Platform 14 is provided with stops 15 or other indexing means for aligning thereon a device 16 to be inspected. In particular the device 16 is illustrated herein in the form of a printed circuit board, it being understood that other precision devices may be similarly positioned for inspection.

More particularly device 16 is positioned by stops 15 to align a bore 17 therein over opening 13. Bore 17 may include through plating or other form of coating, the integrity of which is to be visually inspected. To accomplish this inspection the end of probe 11 is cut along a 45° surface cut-off forming an inclined end surface 20 which may be coated, plated or finished to provide a reflective plane. The central axis of probe 11 may then be aligned under the viewing end of a microscope 21 provided with an annular light source 22 thereabout. The light source 22 then disperses light L into the interior of bore 17 which is then reflected by the end mirror 20 into the microscope 21. Thus the walls of bore 17 may be visually examined, both for integrity and surface finish.

In order to permit translation of probe 11 both axially and in azimuth the mount assembly 12 is provided with two rotary input shafts 31 and 32, shaft 31 extending through a frame 33 to terminate at the other end in a bevel gear 38 aligned to engage gear 34. Thus shaft 37 may be translated in axial translation through gear 38, a downward spring bias therefor being provided by a helical spring 41 surrounding shaft 37 between the lower edge of gear 38 and a stop 42. Gear 38, in turn, is pressed into engagement by a spring washer 43 abutting the underside of extension 35. Similarly gear 34 may be provided with axial displacement features, once more biased for engagement by a spring washer 45. To provide for the upward forcing function the lower end of shaft 37 includes a hemispherical seat supported on a ball roller 47 opposed by a cam 48 on the end of shaft 32.

With this arrangement both vertical and angular manipulation of shaft 37 is possible thus allowing for the necessary freedom of movement of the probe 11 removably installed on the upper end thereof. This manipulation may be performed manually by way of turning knobs 51 and 52 mounted on shafts 31 and 32 respectively or may be automated by powered devices shown in FIG. 4.

Figure 4:
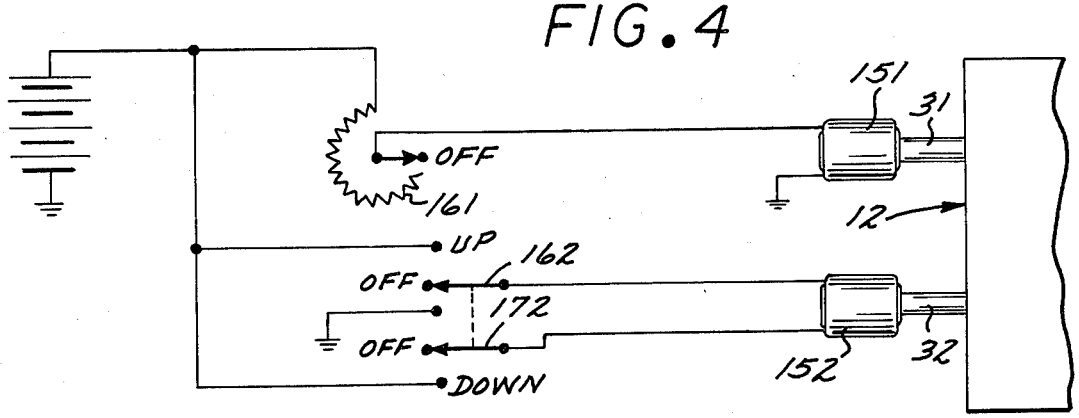
FIG. 4 is a circuit schematic illustrating an alternative implementation for articulating the cylindrical probe.

More specifically, as shown in FIG. 4 shaft 31 is provided with a servomotor 151 driven in rotation by a potentiometer 161 and shaft 32 may be driven by a motor 152 connected to two switches 162 and 172 for up and down articulation.

It is to be understood that the foregoing device may be used with various inspection tasks, in each instance the accomodation being made by selection of probe size or sealing of the assembly.

Obviously many modifications and changes can be made to the foregoing description without departing from the spirit of the invention. It is therefore intended that the scope of the invention be determined solely on the claims appended hereto.

What is claimed is:

1. An assembly for visually inspecting light reflecting cylindrical surfaces that define transverse bores in devices of like demensions, which devices have sidewalls and flat bottom surfaces, said assembly including:
    a. a horizontal platform having an upper surface on which said bottom surface of one of said devices rests, said platform having a transverse opening therein;
    b. stop means on said platform that when engaged by said sidewalls of one of said devices dispose said bore thereof in vertical alignment with said transverse opening;
    c. a tubular microscope disposed a substantial distance above said platform and axially aligned with said opening;
    d. light emitting means for illuminating one of said cylindrical surfaces when one of said devices is disposed on said platform with said bore therein axially aligned with said opening in said platform;
    e. an elongate probe of smaller diameter than that of said bore that is axially aligned in a vertical position with said bore and opening, said probe including a lower end and an upper end, said upper end being light reflective and angularly disposed;
    f. a vertical shaft that has an upper end and a lower end, both of which are disposed below said platform, with said lower end of said probe removably secured to said upper end of said shaft;
    g. first means that rotatably support said shaft for longitudinal movement towards and away from said platform;
    h. second means that at all times tend to maintain said shaft in a first position where said light reflective upper end of said probe is disposed below said upper surface of said platform;
    i. third means for moving said shaft upwardly to a second position where said light reflective upper end of said probe is within said bore to permit a section of the surface of said device that defines said bore to be viewed in said microscope; and
    j. fourth means for rotating said shaft and probe to permit the entire surface that defines said bore to be sequentially viewed when said shaft is in said second position and said shaft is rotated through three hundred and sixty degrees.

2. An assembly as defined in claim 1 in which said light means directs at least one beam of light downwardly onto said cylindrical surface of said device resting on said platform and in engagement with said stop means.

3. An assembly as defined in claim 1 in which said first means is a mount assembly disposed in a fixed position below said platform and said third biased spring.

4. An assembly as defined in claim 1 in which said third means includes:
    k. a first horizontal shaft rotatably supported in said mount assembly;
    l. a cam secured to said first shaft and disposed below said vertical shaft, said biased spring at all times maintaining said lower end of said vertical shaft in contact with said cam, with said first shaft and cam when rotated moving said vertical shaft between said first and second positions.

5. An assembly as defined in claim 4 in which said fourth means includes:
    m. a second horizontal shaft rotatably supported in said mount assambly;
    n. a first gear rigidly secured to said second shaft and adjacently disposed to said vertical shaft; and
    o. a second gear that is slidably engaged by said vertical shaft and engages said first gear, said second horizontal shaft when rotated concurrently rotating said first and second gears and said vertical shaft and probe to permit the latter to rotate through three hundred and sixty degrees.

6. An assembly as defined in claim 5 which in addition includes:
    p. electrically operated power means for selectively driving said first and second horizontal shafts.

* * * * *